United States Patent

Armour et al.

Patent Number: 5,569,654
Date of Patent: Oct. 29, 1996

[54] BENZODIAZEPINONES

[75] Inventors: Duncan R. Armour; Philip C. Box; Pritom Shah, all of Hertfordshire, Great Britain

[73] Assignee: Glaxo Group Limited, London, England

[21] Appl. No.: 446,728

[22] PCT Filed: Dec. 2, 1993

[86] PCT No.: PCT/EP93/03381

§ 371 Date: Jun. 5, 1995

§ 102(e) Date: Jun. 5, 1995

[87] PCT Pub. No.: WO94/13648

PCT Pub. Date: Jun. 23, 1994

[30] Foreign Application Priority Data

Dec. 5, 1992 [GB] United Kingdom ............... 9225492

[51] Int. Cl.⁶ .................. C07D 243/14; A61K 31/55
[52] U.S. Cl. ............................... 514/221; 540/517
[58] Field of Search ..................... 514/221; 540/517

[56] References Cited

FOREIGN PATENT DOCUMENTS

| | | | |
|---|---|---|---|
| 0434369 | 6/1991 | European Pat. Off. | 514/221 |
| 0514133 | 11/1992 | European Pat. Off. | 540/517 |
| WO93/14074 | 7/1993 | WIPO | 514/221 |

*Primary Examiner*—Robert T. Bond
*Attorney, Agent, or Firm*—Bacon & Thomas

[57] ABSTRACT

Compounds of general formula (I)

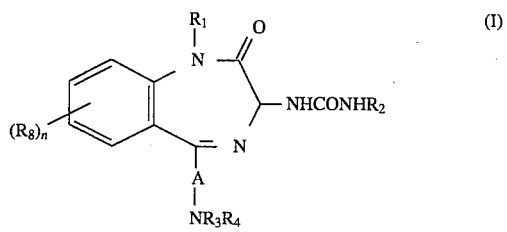

and physiologically acceptable salts thereof;
wherein $R_1$ represents $CH_2CONR_5R_6$ or $CH_2COR_7$;
$R_2$ represents a phenyl group optionally substituted by 1 or 2 substituents selected from halogen, alkyl, nitro, cyano, trifluoromethyl, trifluoromethoxy, alkylthio, alkylsulphinyl, alkylsulphonyl, amino, substituted amino, hydroxy, alkoxy, methylenedioxy, alkoxycarbonyl, oxazolyl or oxadiazolyl;
A represents a $C_{1-4}$ straight or branched alkylene chain;
$R_3$ and $R_4$ independently represent hydrogen or $C_{1-4}$alkyl or $R_3$ and $R_4$ together with the nitrogen atom to which they are attached form a saturated 5–7 membered heterocyclic ring, which ring may contain an additional heteroatom selected from oxygen, sulphur or nitrogen;
$R_5$ represents hydrogen or $C_{1-4}$alkyl;
$R_6$ represents $C_{1-4}$alkyl or phenyl, optionally substituted by halogen, or $R_5$ and $R_6$ together with the nitrogen atom to which they are attached represent a saturated 5 to 7 membered heterocyclic ring which may be optionally substituted by 1 or 2 methyl groups or fused to a benzene ring;
$R_7$ represents a group selected from $C_{1-4}$alkyl, or optionally substituted phenyl;
$R_8$ represents hydrogen or a halogen atom;
n is zero, 1 or 2, are antagonists of gastrin and CCK.

12 Claims, No Drawings

BENZODIAZEPINONES

This invention relates to novel amine derivatives, to processes for their preparation, to pharmaceutical compositions containing them and to their use in medicine.

In particular the invention relates to 5-aminoalkyl-1,4-benzodiazepine derivatives which modulate the effects of gastrin and/or cholecystokinin (CCK) in mammals.

Thus the invention provides compounds of general formula (I)

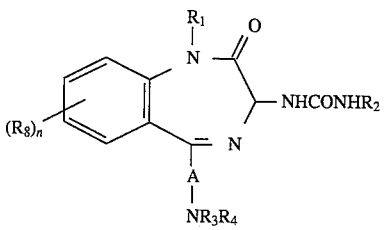

and physiologically acceptable salts thereof;
wherein $R_1$ represents $CH_2CONR_5R_6$ or $CH_2COR_7$; $R_2$ represents a phenyl group optionally substituted by 1 or 2 substituents selected from halogen, alkyl, nitro, cyano, trifluoromethyl, trifluoromethoxy, alkylthio, alkylsulphinyl, alkylsulphonyl, amino, substituted amino, hydroxy, alkoxy, methylenedioxy, alkoxycarbonyl, oxazolyl or oxadiazolyl;
A represents a $C_{1-4}$ straight or branched alkylene chain;
$R_3$ and $R_4$ independently represent hydrogen or $C_{1-4}$alkyl or $R_3$ and $R_4$ together with the nitrogen atom to which they are attached form a saturated 5-7 membered heterocyclic ring, which ring may contain an additional heteroatom selected from oxygen, sulphur or nitrogen;
$R_5$ represents hydrogen or $C_{1-4}$alkyl;
$R_6$ represents $C_{1-4}$alkyl or phenyl, optionally substituted by halogen, or $R_5$ and $R_6$ together with the nitrogen atom to which they are attached represent a saturated 5 to 7 membered heterocyclic ring which may be optionally substituted by 1 or 2 methyl groups or fused to a benzene ring;
$R_7$ represents a group selected from $C_{1-4}$alkyl, or optionally substituted phenyl;
$R_8$ represents hydrogen or a halogen atom;
n is zero, 1 or 2.

It will be appreciated that compounds of formula (I) possess at least one asymmetric carbon atom (namely the carbon atom occupying the 3-position of the diazepine ring) and the compounds of the invention thus include all stereoisomers and mixtures thereof including the racemates.

In the compounds of formula (I) the term alkyl as a group or part of a group refers to a straight or branched chain alkyl group containing 1 to 4 carbon atoms and includes methyl, ethyl, n-propyl, isopropyl, n-butyl, isobutyl, or tert-butyl.

Halogen in the definition of compounds of formula (I) may represent a fluoro, chloro, bromo or iodo substituent.

When $R_7$ represents $C_{1-4}$alkyl examples of suitable groups include t-butyl.

When $R_7$ represents optionally substituted phenyl examples of suitable groups includes phenyl or phenyl substituted by a methyl group e.g. 2-methylphenyl.

When $NR_5R_6$ represents a saturated 5- to 7-membered heterocyclic ring this may be for example pyrrolidino, piperidino or hexamethylenimino which rings may be substituted by one or two methyl groups, such as 2,5-dimethyl pyrrolidino, 3,3 dimethylpyrrolidino, 3,3 dimethylpiperidino or 4,4-dimethylpiperidino.

When $NR_5R_6$ represents a saturated heterocyclic ring fused to a benzene ring this may be for example a group selected from

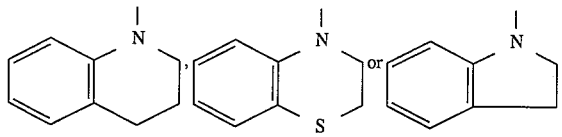

When $NR_3R_4$ represents a 5-7 membered saturated heterocyclic ring this may be for example pyrrolidino, piperidino, hexamethylenimino, morpholino, thiomorpholino and oxides thereof, piperazino or an N-substitued derivative thereof e.g. N-methyl piperazino or N-alkoxycarbonyl piperazino.

When $R_3$ and $R_4$ represent $C_{1-4}$alkyl examples of suitable groups include methyl, ethyl, ispropyl, propyl or n-butyl.

The alkylene chain A in the compounds of formula (I) is preferably a straight chain alkylene such as methylene, ethylene, propylene or butylene.

When $R_8$ represents halogen examples of suitable groups include chlorine or fluorine.

The term oxazolyl refers to a 1,3 oxazolyl group which is linked to the rest of the molecule via the carbon atom in the 2 or 5 position.

The term oxadiazolyl refers to a 1,2,4 oxadiazolyl group which is linked to the rest of the molecule via the carbon atom in the 3 or 5 position.

In compounds of formula (I) the term substituted amino means $C_{1-4}$alkylamino, e.g. isopropylamino, $diC_{1-4}$alkylamino e.g. dimethylamino, $C_{1-4}$alkanoylamino or $C_{1-4}$alkoxycarbonylamino e.g. t-butoxycarbonylamino.

When $R_2$ is phenyl containing a single substituent this is preferably in the meta or para position.

A preferred class of compounds of formula (I) include those wherein $R_1$ represents the group $CH_2CONR_5R_6$. Within this class particularly preferred compounds are those wherein $R_5$ represents methyl or ethyl and $R_6$ represents phenyl or phenyl substituted by a halogen atom such as 2-chlorophenyl or more particularly 4-fluorophenyl or $NR_5R_6$ represents a saturated heterocyclic ring selected from pyrrolidino, 2,5-dimethylpyrrolidino, 3,3-dimethylpyrrolidino, piperidino, 3,3-dimethylpiperidino, or 1-tetrahydroquinolino.

A further preferred class of compounds of formula (I) are those wherein A represents a methylene or ethylene chain and more particularly a methylene chain.

Compounds of formula (I) wherein $NR_3R_4$ represents a 5-7 membered saturated heterocyclic ring selected from pyrrolidino, piperidino, hexamethylenimino, morpholino, thiomorpholino or N-methyl piperazino represent a further preferred class of compounds of formula (I). From within this class particularly preferred compounds are those wherein $NR_3R_4$ represent morpholino.

Another preferred class of compounds of formula (I) are those wherein $R_2$ is a phenyl group optionally substituted by one or two groups selected from halogen e.g. fluorine, alkyl, e.g. methyl, alkoxy, e.g. methoxy, amino, cyano, hydroxy-oxazolyl, trifluoromethyl, or 1,2,4-oxadiazol-3-yl. From within this class of compounds those wherein $R_2$ is a phenyl group substituted by fluorine, oxazol-5-yl or more especially methoxy are particularly preferred.

A further preferred class of compounds of formula (I) are those wherein $R_8$ is fluorine or chlorine or more particularly hydrogen.

A preferred group of compounds of formula (I) are those wherein $R_1$ is the group $CH_2CONR_5R_6$ wherein $R_5$ and $R_6$ are as defined above, $R_8$ represents hydrogen, the group A and $NR_3R_4$ have the meanings defined above and $R_2$ is a phenyl group optionally substituted by 1 or 2 substituents selected from halogen, alkyl, nitro, cyano, trifluoromethyl, trifluoromethoxy, alkylthio, alkylsulphinyl, alkylsulphonyl, amino, substituted amino, hydroxy, alkoxy, methylenedioxy or alkoxycarbonyl.

A further preferred group of compounds of formula (I) are those wherein $R_1$ represents the group $CH_2CONR_5R_6$. A represents a methylene chain, $NR_3R_4$ represents a saturated 5–7 membered heterocyclic ring which may contain an additional heteroatom selected from oxygen, sulphur or nitrogen. From within this group particularly preferred compounds include those wherein $R_5$ is methyl or ethyl and $R_6$ is phenyl optionally substituted by fluorine or chlorine or $NR_5R_6$ represents a pyrrolidino, 2,5-dimethylpyrrolidino, 3,3-dimethylpyrrolidino, piperidino, 3,3-dimethylpiperidino, or 1-tetrahydroquinolino, $R_2$ represents phenyl optionally substituted by one or 2 groups selected from fluorine, methyl, methoxy, trifluoromethyl amino, cyano, hydroxy, oxazol-5-yl or 1,2,4-oxadiazol-3-yl and $R_8$ represents hydrogen or $R_8$ represents fluorine or chlorine and n is 1.

Particularly preferred compounds of the invention include
2-{3-[3-(3-Methoxy-phenyl)-ureido]-5-morpholin-4-ylmethyl-2 -oxo-2,3-dihydro-benzo[e][1,4]diazepin-1-yl}-N-methyl-N-phenyl-acetamide;
N-Methyl-2-[5-morpholin-4-ylmethyl-2-oxo-3-(3-phenylureido)-2,3-dihydro-benzo[e][1,4]diazepin-1-yl]-N-phenyl-acetamide;
N-Methyl-2-{5-morpholin-4-ylmethyl-2-oxo-3-[3-(3-trifluoromethyl-phenyl)-ureido]- 2,3-dihydro-benzo[e][i,4]diazepin-1-yl}-N-phenyl-acetamide;
2-{3-[3-(3-Cyano-phenyl)-ureido]-5-morpholin-4-ylmethyl-2-oxo-2,3-dihydro-benzo[e][1,4]diazepin-1-yl}-N-methyl-N-phenyl-acetamide;
1-[5-(Morpholin-4-yl-methyl)-2-oxo-1-(2-oxo-2-pyrrolidin-1-yl-ethyl)-2,3 -dihydro1H-benzo[e][1,4]diazepin-3-yl]-3-(3-oxazol-5-yl-phenyl)-urea;
N-Ethyl-N-(4-fluoro-phenyl)-2-{3-[3-(4-fluoro-phenyl)-ureido]-5 -(morpholin-4-ylmethyl)-2-oxo-2,3-dihydrobenzo[e][1,4]diazepin-1-yl}-acetamide;
and the enantiomers thereof; and physiologically acceptable salts thereof.

The physiologically acceptable salts of the compounds of formula (I) include conventional salts formed for example from pharmaceutically acceptable inorganic or organic acids as well as quaternary ammonium acid addition salts. Examples of suitable salts include hydrochloric, hydrobromic, sulfuric, phosphoric, nitric, perchloric, fumaric, acetic, propionic, succinic, glycolic, formic, lactic, maleic, tartaric, citric, pamoic, malonic, hydroxymaleic, phenylacetic, glutamic, benzoic, salicylic, fumaric, toluenesulphonic, methanesulphonic, naphthalene-2-sulphonic, benzenesulphonic and the like. Other acids such as oxalic, while not in themselves pharmaceutically acceptable, may be useful in the preparation of salts useful as intermediates in obtaining the compounds of the invention and their pharmaceutically acceptable salts.

References hereinafter to a compound according to the invention includes both compounds of formula (I) and their pharmaceutically acceptable salts and solvates.

Compounds of the invention modulate the effect of gastrin and/or CCK in mammals. In particular compounds of the invention are antagonists of gastrin and/or CCK.

Compounds of the invention have been shown to be antagonists of gastrin as demonstrated by their ability to inhibit pentagastrin-stimulated acid secretion from rat isolated gastric mucosa using the procedure described by J. J. Reeves and R. Stables in Br. J. Pharmac., 1985 86, p.677–684.

Compounds of the invention have also been shown to be antagonists of CCK, particularly at CCK-B receptors as demonstrated for example by the compound's ability to inhibit the contractile actions of CCK-4 in the presence of a CCK-A antagonist, in the guinea-pig isolated ileum longitudinal muscle-myenteric plexus.

The preparation and use of guinea-pig isolated ileum longitudinal muscle-myenteric plexus has been described by K-H Buchheit et al in Nauyn-Schmeideberg's Arch. Pharmacol., (1985), 329, p36–41 and by V. L. Lucaites et al (1991) in J. Pharmacol. Exp. Ther., 256, 695–703.

The affinity of the compound of the invention for the CCK-B receptor has also been determined using the guinea pig codex assay as described by G Dal Fornoto et al J. Pharmacol Exp. Ther., 261 1056–1063, 1992.

The compounds of the invention are therefore useful for the treatment and/or prevention of disorders in mammals, especially humans, where modification of the effects of gastrin or CCK is of therapeutic benefit. Thus the compounds of the invention are useful for the treatment of gastrointestinal disorders especially those where there is an advantage in lowering gastric acidity. Such disorders include peptic ulceration, reflux oesophagitis and Zollinger Ellison syndrome. They may also be useful for the treatment of gastrointestinal disorders such as irritable bowel syndrome, excess pancreatic secretion, acute pancreatitis, motility disorders, antral G cell hyperplasia, fundic mucosal hyperplasia or gastrointestinal neoplasms. The compounds of the invention are also useful for the treatment of central nervous system disorders where CCK and/or gastrin are involved. For example anxiety disorders (including panic disorder, agoraphobia, social phobia, simple phobia, obsessive compulsive disorders, post traumatic stress disorder, and general anxiety disorder), depression, tardive dyskinesia, Parkinson's disease or psychosis. They may also be useful for the treatment of dependency on drugs or substances of abuse and withdrawal, Gilles de la Tourette syndrome, or dysfunction of appetite regulatory systems; as well as the treatment of certain tumours of the lower oesophagus, stomach, intestines and colon. Compounds of the invention are also useful for directly inducing analgesia, or enhancing opiate or non-opiate mediated analgesia, as well as anaesthesia or loss of the sensation of pain.

The invention therefore provides a compound of formula (I) or a pharmaceutically acceptable salt or solvate thereof for use in therapy, in particular in human medicine, According to another aspect the invention provides the use of a compound of formula (I) or a pharmaceutically acceptable salt or solvate thereof for the manufacture of a medicament for the treatment of conditions where modification of the effects of gastrin and/or CCK is of therapeutic benefit.

According to a further aspect of the invention we provide a method for the treatment of a mammal, including man, in particular in the treatment of conditions where modification of the effects of gastrin and/or CCK is of therapeutic benefit which method comprises administering an effective amount of a compound of formula (I) or a pharmaceutically acceptable salt or solvate thereof to the patient.

It will be appreciated by those skilled in the art that reference herein to treatment extends to prophylaxis as well as the treatment of established diseases or symptoms.

It will further be appreciated that the amount of a compound of the invention required for use in treatment will vary with the nature of the condition being treated and the age and the condition of the patient and will be ultimately at the discretion of the attendant physician or veterinarian. In general however doses employed for adult human treatment will typically be in the range of 1–2000 mg per day e.g 10–500 mg per day.

The desired dose may conveniently be presented in a single dose or as divided doses administered at appropriate intervals, for example as two, three, four or more sub-doses per day.

Compounds of the invention which antagonise the function of CCK in animals, may also be used as feed additives to increase the food intake in animals in daily dosages of around 1 mg/kg to 10 mg/kg.

While it is possible that, for use in therapy, a compound of the invention may be administered as the raw chemical it is preferable to present the active ingredient as a pharmaceutical formulation.

The invention thus further provides a pharmaceutical formulation comprising a compound of formula (I) or a pharmaceutically acceptable salt thereof together with one or more pharmaceutically acceptable carriers therefor and, optionally, other therapeutic and/or prophylactic ingredients. The carrier(s) must be 'acceptable' in the sense of being compatible with the other ingredients of the formulation and not deleterious to the recipient thereof.

The compositions of the invention include those in a form especially formulated for oral, buccal, parenteral, implant, or rectal administration. Oral administration is preferred.

Tablets and capsules for oral administration may contain conventional excipients such as binding agents, for example, syrup, acacia, gelatin, sorbitol, tragacanth, mucilage of starch or polyvinylpyrrolidone; fillers, for example, lactose, sugar, microcrystalline cellulose, maize-starch, calcium phosphate or sorbitol; lubricants, for example, magnesium stearate, stearic acid, talc, polyethylene glycol or silica; disintegrants, for example, potato starch or sodium starch glycollate, or wetting agents such as sodium lauryl sulphate. The tablets may be coated according to methods well known in the art. Oral liquid preparations may be in the form of, for example, aqueous or oily suspensions, solutions emulsions, syrups or elixirs, or may be presented as a dry product for constitution with water or other suitable vehicle before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminium stearate gel or hydrogenated edible fats; emulsifying agents, for example, lecithin, sorbitan mono-oleate or acacia; non-aqueous vehicles (which may include edible oils), for example, almond oil, fractionated coconut oil, oily esters, propylene glycol or ethyl alcohol; and preservatives, for example, methyl or propyl p-hydroxybenzoates or ascorbic acid. The compositions may also be formulated as suppositories, e.g. containing conventional suppository bases such as cocoa butter or other glycerides.

For buccal administration the composition may take the form of tablets or lozenges formulated in conventional manner.

The composition according to the invention may be formulated for parenteral administration by injection or continuous infusion. Formulations for injection may be presented in unit dose form in ampoules, or in multi-dose containers with an added preservative. The compositions may take such forms as suspensions, solutions, or emulsions in oily or aqueous vehicles, and may contain formulatory agents such as suspending, stabilising and/or dispersing agents. Alternatively the active ingredient may be in powder form for constitution with a suitable vehicle, e.g. sterile, pyrogen-free water, before use.

The composition according to the invention may also be formulated as a depot preparation. Such long acting formulations may be administered by implantation (for example subcutaneously or intramuscularly) or by intramuscular injection. Thus for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

The compositions according to the invention may contain between 0.1–99% of the active ingredient, conveniently from 30–95% for tablets and capsules and 3–50% for liquid preparations.

Compounds of general formula (I) and salts thereof may be prepared by the general methods outlined hereinafter. In the following description, the groups $R_1$–$R_8$ are as defined for the compounds of formula (I) unless otherwise stated.

Compounds of formula (I) may be prepared by the reaction of a compound of formula (II)

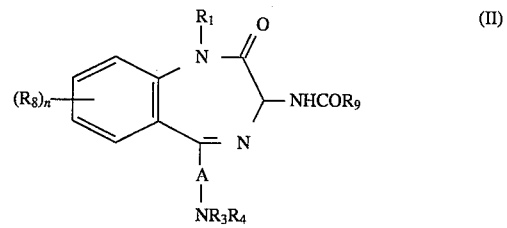

(II)

wherein $R_1$, $R_3$, $R_4$, $R_8$ and A have the meaning given in formula (I) and $R_9$ is a leaving group, with an amine $R_2NH_2$ wherein $R_2$ has the meanings given above in formula (I). Examples of suitable leaving groups $R_9$ include 1-imidazole, or an optionally substituted phenoxy group.

The reaction conveniently takes place in a suitable solvent such as a halogenated hydrocarbon (e.g. dichloromethane) an ether (e.g. tetrahydrofuran) or an amide (e.g. N,N-dimethylformamide) or mixtures thereof at a temperature ranging from room temperature to the reflux temperature of the solvent.

In a particular aspect of the process with a compound of formula (II) wherein $R_9$ is a 1-imidazole group, this compound may be formed in situ, in which case the amine $R_2NH_2$ will be reacted with the compound of formula (III)

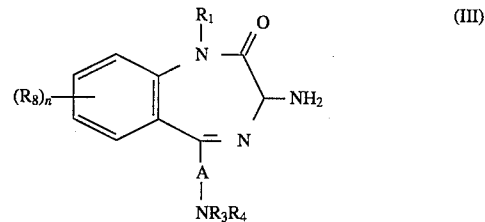

(III)

in the presence of carbonyl diimidazole under the aforementioned conditions.

Compounds of formula (II) may be prepared from compounds of formula (III). Thus a compound of formula (II) wherein $R_9$ is 1-imidazole may be prepared by reacting a compound of formula (III) with carbonyldiimidazole in a suitable solvent such as a halogenated hydrocarbon (e.g. dichloromethane) or an ether (e.g. tetrahydrofuran) at a temperature ranging from 0° to 80° C., conveniently at room temperature.

Compounds of formula (II) wherein $R_1$, $R_3$, $R_4$ and A have the meanings defined in formula (I) and $R_9$ is an optionally substituted phenoxy group may be prepared by reaction of a compound of formula (III) with the appropriate haloformate R₉COHal wherein Hal is chlorine or bromine. The reaction is preferably carried out in the presence of a base such as a tertiary amine e.g. triethylamine or pyridine, and in a solvent such as a halohydrocarbon e.g. dichloromethane.

Compounds of formula (I) may also be prepared by reacting a compound of formula (III) wherein $R_1$, $R_3$, $R_4$ and A have the meanings defined above for formula (I) with the isocyanate $R_2NCO$ or carbamoyl chloride $R_2NHCOCL$ (wherein $R_2$ has the meaning defined in formula (I)). The reaction conveniently takes place in the presence of a suitable solvent such as a halohydrocarbon (e.g. dichloromethane), an ether (e.g. tetrahydrofuran) or a nitrile (e.g. acetonitrile) or a mixture thereof at a temperature in the range of 0° to 80° C.

The compounds of formula (III) may be prepared by hydrogenolysis of the corresponding benzyl carbamate of formula (IV), in which $R_1$ and $R_2$ have the meanings defined above.

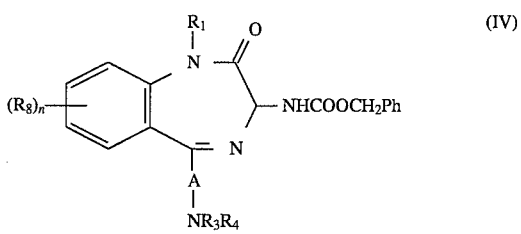

Hydrogenolysis may be effected using catalytic hydrogenation conditions with a suitable metal catalyst such as palladium on carbon in a solvent such as an alcohol e.g. methanol.

Conveniently the reaction is carried out at a temperature within the range 20°–100° C. and in the presence of ammonium formate.

The compounds of formula (IV) may be prepared by alkylation of the corresponding carbamates of formula (V)

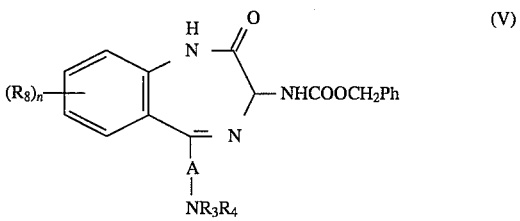

The alkylation reaction is preferably carried out by treating a compound of formula (V) with a strong base such as sodium hydride in a polar aprotic solvent, such as N,N-dimethylformamide, followed by reaction with an alkylating agent $R_1L$ wherein $R_1$ has the meanings defined above in formula (I) and L is a leaving group such as a halogen e.g. chlorine or bromine.

The reaction is preferably carried out at a temperature within the range −30° to 40° C.

The compound of formula (V) may be prepared by cyclisation of the ketone derivative (VI)

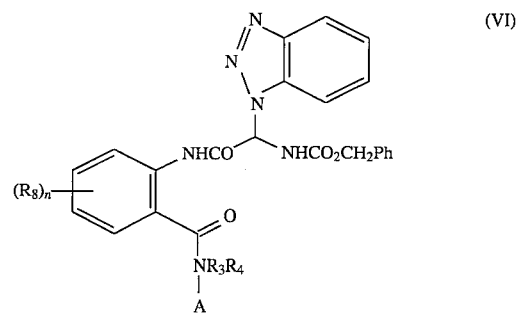

The cyclisation may be carried out by treating the compound (VI) with ammonia in a suitable solvent such as an ether e.g. tetrahydrofuran followed by reaction with sodium acetate in glacial acetic acid.

Compounds of formula (IV) wherein A is a methylene group may also be prepared by reaction of the compound of formula (VII) wherein $R_1$ is as defined in formula (I)

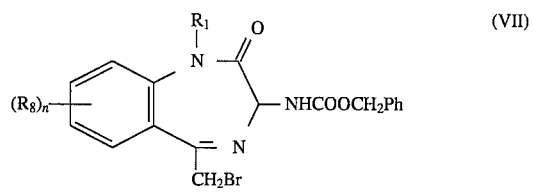

with an amine $R_3R_4NH$, preferably in a solvent such as halohydrocarbon e.g. dichloromethane.

Compounds of formula (VII) may be prepared by bromination of the compound of formula (VIII)

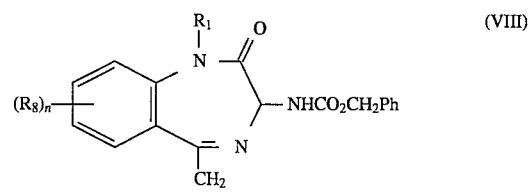

The bromination reaction may be carried out using a reagent such as N-bromosuccinimide or 5,5-dibromobarbituric acid.

Compounds of formula (IV) wherein A is an ethylene group may be prepared from a compound of formula of (VIII) with the amine $HNR_3R_4$ and formaldehyde under conventional Mannich reaction conditions.

The compounds of formula (VIII) may be prepared by alkylation of the compound of formula (IX)

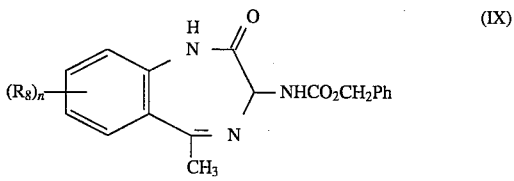

using the same conditions as that described above for preparing the corresponding compound of formula (IV) from compound (V).

The compounds of formula (VI) may be prepared by condensation of the amino ketone (X) with the benzotriazole derivative (XI)

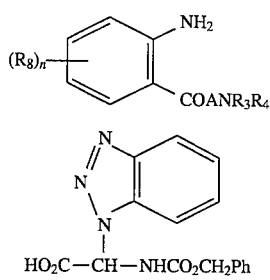

(X)

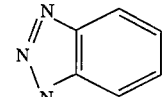

(XI)

HO₂C—CH—NHCO₂CH₂Ph

The condensation reaction may be carried out using conventional procedures, for example by the reaction of (X) with (XI) in the presence of dicyclohexylcarbodiimide in a solvent such as tetrahydrofuran.

The compounds of formula (X) are either known compounds or may be prepared by analogous methods described for preparing known compounds.

Compounds of formula (I) wherein A represents a methylene group may also be prepared by reaction of the bromomethyl derivative (XII)

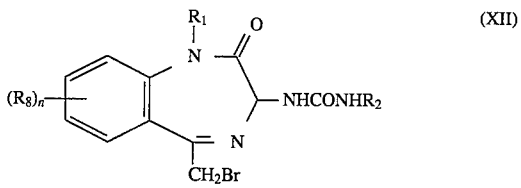

(XII)

wherein $R_1$ and $R_2$ are as defined in formula (I) with the amine $R_3R_4NH$, wherein $R_3$ and $R_4$ are as defined in formula (I). The reaction is preferably carried out in an aprotic solvent such as a halohydrocarbon e.g. dichloromethane. The bromomethyl derivatives (XII) may be prepared by bromination of the corresponding methyl compound (XIII)

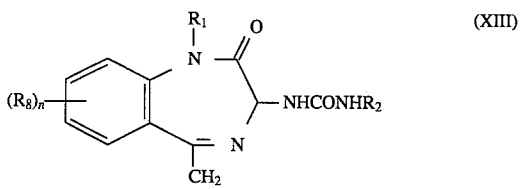

(XIII)

The bromination reaction may be carried out using a reagent such as 5,5dibromobarbituric acid in a solvent such as a halohydrocarbon e.g. dichloromethane, or chloroform or mixtures thereof.

The methyl derivative (XIII) may be prepared from the corresponding intermediate (VIII) using the general procedures described above for converting the compound of formula (IV) into a compound of formula (I).

Compounds of the invention may be converted into other compounds of the invention. Thus compounds of formula (I) wherein $R_2$ is a phenyl group substituted by amino may be prepared from the corresponding compound wherein $R_2$ is a phenyl group substituted by an alkoxycarbonylamino group by conventional means such as acid hydrolysis. For example compounds wherein $R_2$ is phenyl substituted by amino may be prepared by reaction of the corresponding t-butylcarbonylamino compound with trifluroacetic in a suitable solvent such as dichloromethane.

Acid addition salts of compounds of formula (I) may be prepared by reaction with the appropriate physiologically acceptable acid in a suitable solvent followed if necessary by addition of suitable non solvent.

The compounds of formulae (II), (III), (IV), (V), (VI) and (VII) are novel and form further aspects of the invention.

In general, the compounds $R_2NH_2$, $R_2NCO$ or $R_2HNCOCL$ are either known or may be prepared according to methods used for the preparation of known compounds. For example the amines $R_2NH_2$ may be prepared by reduction of the corresponding nitro compounds $R_2NO_2$. The reduction may be effected for example by catalytic hydrogenation using a suitable metal catalyst such as palladium on carbon in a suitable solvent such as an alcohol (e.g. ethanol) at room temperature.

Compounds of formula (I) contain at least one asymmetric carbon atom, namely the carbon atom of the diazepine ring to which the substituted urea grouping is attached. Specific enantiomers of the compounds of formula (I) may be obtained by resolution of the racemic compound using conventional procedures such as salt formation with a suitable optically active acid or by the use of chiral H.P.L.C. Alternatively the required enantiomer may be prepared from the corresponding enantiomeric amine of formula (III) using any of the processes described above for preparing compounds of formula (I) from the amine (III). The enantiomers of the amine (III) may be prepared from the racemic amine (III) using conventional procedures such as salt formation with a suitably optically active acid. Alternatively the racemic amine (III) may be reacted with an optically active carbonate ester to yield an optically active carbamate thereof. The resultant diastereoisomers may then be separated by conventional means. Each separate diastereosiomeric carbamate may then be converted into the corresponding enantiomeric amine (III) by conventional processes.

The following examples, which are non-limiting, illustrate the invention. Temperatures are in °C. "Dried" refers to drying with anhydrous $Mg_2SO_4$. All chromatography was carried out on silica gel. The following abbreviations are used. T.I.c. —thin layer chromatography; CDI—carbonyldiimidazole; DCM—dichloromethane; DE—Diethyl ether; THF—tetrahydrofuran; DMF—N,N-dimethylformamide; EA—ethyl acetate; McOH—methanol; $CHCl_3$—chloroform; NaH—sodium hydride; ir—infra red spectra determined as a mull in mineral oil unless otherwise stated.

INTERMEDIATE 1

Phenylmethyl
[2[(2-acetylphenyl)amino]-1-[(1-methylethyl)thio]-2-oxoethyl]carbamate A suspension of [(1-methylethyl)thio]-[(phenylmethoxy)carbonyl]amino]acetic acid (10.49 g) in dry DCM (175 ml) at 0° under nitrogen was treated with 4-methylmorpholine (3.93 g) followed by the dropwise addition of isobutyl chloroformate (5.31 g). The mixture was stirred at 0° for 40 min and a solution of 2-aminoacetophenone (5.00 g) in dry DCM (60 ml) was added dropwise. The mixture was stirred at 0° for 1 h then at 23° for 18 h. The mixture was washed with 2N hydrochloric acid, 2N sodium carbonate solution, saturated brine and dried. Solvent evaporation in vacuo gave the title compound (14.82 g) which was used without further purification.

T.I.c. (1:1 DE-hexane) Rf 0.3

INTERMEDIATE 2

Phenylmethyl [2,3-dihydro-5-methyl-2-oxo-1H-1,4-benzodiazepin-3yl]carbamate

Ammonia gas was passed through a solution of phenylmethyl[2-[(2-acetylphenyl)amino]-1-[(1-methylethyl)thio]-2-oxoethyl]carbamate (14.74 g) in dry THF (250 ml) at 0° for 0.5 h. Mercury (II) chloride (10.00 g) was added and the mixture was rapidly stirred for 6 h whilst continuing to pass ammonia gas through the mixture. The mixture was filtered through hyflo and the solvent removed from the filtrate by evaporation in vacuo. The residue was treated with acetic acid (290 ml) and sodium acetate (13.35 g) and the resulting mixture stirred at 23° for 18 h. The solvent was evaporated in vacuo and the residue was purified by chromatography. Elution with EA gave the title compound (5.70 g).
T.l.c. (3:2 EA-hexane) Rf 0.4

INTERMEDIATE 3

Phenylmethyl [2,3-dihydro-5-methyl-1-[2-(methylphenylamino)-2-oxoethyl]-2-oxo-1H-1,4-benzodiazepin-3-yl]carbamate.

80% Sodium hydride in oil (102 mg) was added to a solution of phenylmethyl [2,3-dihydro-5-methyl-2-oxo-1H-1,4-benzodiazepin-3-yl]carbamate (1.00 g) in dry DMF (10 ml) under nitrogen. The mixture was stirred for 0.5 h at 23° and was treated with a solution of 2-bromo-N-methyl-N-phenylacetamide (707 mg) in dry DMF (1 ml). The mixture was stirred at 23° for 1 h, partitioned between phosphate buffer solution (pH6.5) and EA, the organic phase was washed with water and dried. The solvent was evaporated in vacuo and the residue was purified by chromatography on alumina. Elution with MeOH-DCM (1:50) gave the title compound (568 mg).
T.l.c. (1:50 MeOH-DCM) Rf 0.2

INTERMEDIATE 4

3-Amino-2,3-dihydro-N.5-dimethyl-2-oxo-N-phenyl-1H-1,4-benzo diazepine-1-acetamide A mixture of 5% palladium on carbon (300 mg) and phenylmethyl [2,3-dihydro-5-methyl-1-[2-(methylphenylamino)-2-oxoethyl]-2-oxo-1H-1,4-benzodiazepin-3-yl]carbamate (500 mg) in MeOH-water 4:1(40 ml) at 40° under nitrogen was treated with ammonium formate (201 mg) and the mixture stirred at 40° for 1 h. The mixture was cooled to 23° and was filtered through hyflo. The filtrate was evaporated in vacuo and the residue partitioned between 2 N sodium carbonate solution and chloroform. The organic phase was dried and the solvent evaporated in vacuo. The residue was purified by chromatography, elution with MeOH-DCM (1:9) gave the title compound(302 mg).
T.l.c. (1:9 MeOH-DCM) Rf 0.3

INTERMEDIATE 5

2,3-Dihydro-N.5-dimethyl-2-oxo-N-phenyl-[3[[(3-cyanophenyl)amino]carbonyl]amino]-1H-1,4-benzodiazepine-1-acetamide 3-Cyanophenyl isocyanate (144 mg) was added to a solution of intermediate 4(336 mg) in dichloromethane (10 ml) under nitrogen and the mixture stirred for 4 h. The reaction mixture was filtered to give the title compound (305 mg) as a white solid, m.p. 210°–211°.

INTERMEDIATE 6

2-{5-Bromomethyl-3-[3-(3-cyano-phenyl)-ureido]-2-oxo-2,3-dihydro-benzo[e][1,4]diazepin-1-yl}-N-methyl-N-phenyl-acetamide A solution of intermediate 5 (2.99 g) in dry DCM (300 ml) and CHCl$_3$ (100 ml) at 23° under nitrogen was treated with 5,5-dibromobarbituric acid (0.93 g). After 18 hours silica (Merck 9385; 20 g) was added and the mixture evaporated in vacuo. The mixture was purified by flash chromatography eluting with (1 to 2 to 5%) MeOH in DCM to give the title compound as a white foam (1.89 g), m.p. 100° dec.
T.l.c. (5%MeOH-DCM) Rf 0.29

INTERMEDIATE 7

5-Bromomethyl-2-oxo-2,3-dihydro-1H-benzo-[e]1,4]diazepine-3-carba mic acid benzyl ester.

5,5-Dibromobarbituric acid (5.1 g) was added to a solution of 2,3-dihydro-5-methyl-2-oxo-1H-benzo[e][1,4]-diazepine-3-carbamic acid benzyl ester (11 g) in dry DCM (750 ml) at 23° under nitrogen. The solution grew progressively cloudier and deeper orange over 20 h whereupon silica (50 g) was added and the mixture evaporated to dryness. The residue was chromatographed on silica (Et$_3$N-deactivated, Merck 9385) with 1% MeOH in DCM as eluent to give the title compound (7.1 g) as a pale yellow solid, m.p. 154° dec.
T.l.c. Et$_3$N-deactivated SiO$_2$ (100:1 DCM-MeOH) Rf 0.55

INTERMEDIATE 8

5-Morpholin-4-ylmethyl-2-oxo-2,3-dihydro-1H-benzo[e][1,4]diazepin e-3-carbamic acid benzyl ester Morpholine (7.5 ml) was added to a solution of intermediate 7 (6.9 g) in dry DCM (190 ml) at 23° under nitrogen. After 3 h the cloudy orange mixture was poured into water (200 ml) and the layers separated. The aqueous phase was re-extracted with DCM (150 ml) and the combined, dried organic extracts evaporated. The residue was chromatographed with 2 to 3% MeOH in DCM as eluent to give the title compound (3.38 g) as a beige foam, m.p. 91° dec.
T.l.c. (95:5 DCM-MeOH) Rf 0.28
I.r. 3235; 1698; 1500; 1456; 1241; 1116 cm$^{-1}$

INTERMEDIATE 9

1-(3-Cyano-phenyl)-3-(5-morpholin-4-ylmethyl-2-oxo-2,3-dihydro-1H-benzo[e][1,4]diazepin-3-yl)
-urea A solution of intermediate 8 (3.38 g) in absolute EtOH (160 ml) was hydrogenated at 23° and 1 atmosphere pressure in the presence of 10% palladium on charcoal as catalyst (1 g). After 3 h the mixture was filtered through hyflo and the filtrate evaporated to give a purple foam. A solution of the foam in MeCN (54 ml) was treated with 3-cyanophenyl isocyanate (1.21 g) and after 1 h DE was added to the resulting suspension. The solid was filtered off and dried at 50° in vacuo to give the title compound (1.44 g) as an off-white solid, m.p. 249°–50°.
T.l.c. (9:1 DCM-MeOH) Rf 0.46

INTERMEDIATE 10

1-(3-Cyano-phenyl)-3-[1-(3.3-dimethyl-2-oxo-butyl)-5-methyl-2-oxo-2,3-dihydro-1H-benzo[e][1,4]diazepin-3-yl]-urea 3-Cyanophenyl isocyanate (278 mg) was added to a solution of 3-amino-2,3-dihydro-1-(3,3,-dimethyl-2-oxo-butyl)-5-methyl-2-oxo-1H-1,4-benzodiazepine (500 mg) in dry MeCN (13 ml) at 23° under nitrogen. After 30 min the resulting thick slurry was stirred with DE (5 ml) filtered and the filtercake washed with EA and DE then dried in vacuo at 50° to give the title compound (571 mg) as a white solid, m.p. 246°–7°
T.l.c. (9:1 DCM-MeOH) Rf 0.51
I.r. 3340; 2229; 1719; 1678; 1646; 1557; 1517 cm$^{-1}$

INTERMEDIATE 11

1-[5-Bromomethyl-1-(3,3-dimethyl-2-oxo-butyl)-2-oxo-2,3-dihydro-1H-benzo[e][1,4]diazepin-3-yl]-3-(3-cyano-phenyl)-urea.

5,5-Dibromobarbituric acid (38 mg) was added to a suspension of intermediate 10 (100 mg) in dry DCM (10 ml) at 23° under nitrogen. After 6.5 h, dry THF (4 ml) was added to induce solubility and stirring was continued for 17 h. Silica (2 g) was added to the pale orange solution and the mixture evaporated to dryness. The residue was chromatographed with 0 to 0.25 to 0.5 to 1 to 2% MeOH in DCM as eluent to give the title compound (80 mg) as a white solid, m.p. 135° dec.
T.l.c. (2% MeOH-DCM) Rf 0.23

INTERMEDIATE 12

5-Bromomethyl-1-(methyl-phenyl-carbamoylmethyl)-2-oxo-2,3-dihydro-1 H-benzo[e][1,4]diazepine-3-carbamic acid, benzyl ester A solution of intermediate 3 (200 mg) in DE (5 ml) and chloroform (5 ml) under nitrogen, was treated with 5,5-dibromobarbituric acid (61 mg) and the mixture stirred at 23° for 18 h. MeOH (5 ml) and silica (1 g) were added and the solvent was evaporated in vacuo. The residue was chromatographed with MeOH-DCM (0.2:10) as eluent to give the title compound (175 mg) as a white foam.
T.l.c. (10:0.5 DCM-MeOH) Rf 0.69
I.r. 3418; 3325; 1727; 1670; 1496; 1453 cm$^{-1}$.

INTERMEDIATE 13

1-(Methyl-phenyl-carbamoylmethyl)-5-morpholin-4-ylmethyl-2-oxo-2,3-dihydro-1H-benzo[e][1,4]diazepine-3-carbamic acid, benzyl ester A solution of intermediate 12 (2.75 g) in DCM (50 ml) was treated with morpholine (2.18 g) and the mixture was stirred at 23° under nitrogen for 1 h. The mixture was washed with water (2×40 ml), brine (40 ml) and dried then evaporated in vacuo. The residue was chromatographed with DCM-MeOH (10:0.3) as eluent to give the title compound (2.38 g) as an orange foam.
I.r. (Solution in CHCl$_3$) 3425; 1723; 1670; 1497; 1452; 1394 cm$^{-1}$.

INTERMEDIATE 14

2-(3-Amino-5-morpholin-4-ylmethyl-2-oxo-2,3-dihydro-benzo[e][1,4]diazepin-1-yl)-N-methyl-N-phenyl-acetamide A solution of intermediate 13 (1.82 g) in EtOH (50 ml) was hydrogenated over 10% palladium on carbon (250 mg) at 23° and 1 atmosphere pressure. After 4 h the mixture was filtered through hyflo and the filtrate evaporated to give the title compound (1.35 g) as a pale yellow foam.
T.l.c. (9:1 DCM-MeOH) Rf 0.25
I.r. (Solution in CHCl$_3$) 3395; 1669; 1598; 1497; 1451; 1116 cm$^{-1}$.

INTERMEDIATE 15

R-Carbonic acid (4-nitro-phenyl) ester (1-phenyl-ethyl) ester

A solution of (R)-sec-phenethyl alcohol (500 mg) and pyridine (324 mg) in DCM (15 ml) at 0°–50° under nitrogen was treated dropwise with a solution of 4-nitrophenyl chloroformate (825 mg) in DCM (10 ml). The mixture was allowed to warm to 23° and was stirred for 18 h. The mixture was partitioned between phosphate buffer (pH 6.5) and DCM. The organic phase was washed with 8% sodium bicarbonate solution and was dried (Na$_2$SO$_4$). Solvent evaporation in vacuo gave a residue which was azeotroped with toluene and then purified by chromatography. Elution with EA-hexane (1:9) gave the title compound as a colourless oil (290 mg).
T.l.c. (1:4 EA-hexane) Rf 0.45
I.r. (film) 3086; 2986; 1765; 1526; 1349; 1258; 1220; 1064; 861; 700 cm$^{-1}$.

INTERMEDIATE 16

R-5-Methyl-1-(methyl-phenyl-carbamoylmethyl)-2-oxo-2,3-dihydro-1H-benzo[e][1,4]diazepine-3-carbamic acid 1-phenyl-ethyl ester A solution of intermediate 4 (200 mg) and intermediate 15 (256 mg) in MeCN (14 ml) under nitrogen was treated with Et$_3$N (60 mg) and the mixture was heated under reflux for 18 h. The mixture was cooled to 23° and was partitioned between phosphate buffer (pH 6.5) and EA. The organic phase was dried (Na$_2$SO$_4$) and the solvent evaporated in vacuo. The residue was purified by chromatography, Elution with EA-hexane (7:3) gave the title compound as a white foam (79 mg).
T.l.c. (7:3 EA-Hexane) Rf 0.26
I.r. 3425; 3318; 1724; 1669; 1632; 1596; 1270; 1244; 1206; 1071; 766; 701 cm$^{-1}$.

INTERMEDIATE 17

2-(3-Amino-5-methyl-2-oxo-2,3-dihydro-benzo[e][1,4]diazepin-1-yl)-N-methyl-N-phenyl-acetamide, (Isomer 2)

A solution of intermediate 16 (442 mg) in EtOH (14 ml) was hydrogenated over 10% palladium on carbon (90 mg). After 7 h the mixture was filtered through hyflo and the solvent evaporated in vacuo to give the title compound as a white foam (311 mg).
T.l.c. (1:20 MeOH-DCM) Rf 0.24
I.r. 1660; 1595; 1317; 1275; 1251; 1200; 1122; 964; 770; 724; 702; 558 cm$^{-1}$.

INTERMEDIATE 18

2-{3-[3-(3-Methoxy-phenyl)-ureido]-5-methyl-2-oxo-2,3-dihydro-benzo[e][1,4]diazepin-1yl}-N-methyl-N-phenyl-acetamide, (Isomer 1)

A solution of intermediate 17 (208 mg) in DCM (5 ml) under nitrogen was treated with 3-methoxyphenyl isocyanate (92 mg) and the mixture was stirred for 4 h at 23°. The solvent was evaporated in vacuo and the residue was purified by chromatography. Elution with MeOH-DCM (1:20)

gave the title compound as a white solid (221 mg), m.p. 238°–9°.
T.l.c. (1:20 MeOH-DCM) Rf 0.30
I.r. 3311; 1666; 1637; 1612; 1558; 1523; 1496; 1158; 1036; 766; 701; 557 cm$^{-1}$.

INTERMEDIATE 19

1-(Methyl-phenyl-carbamoylmethyl)-5-(4-methyl-piperazin-1ylmethyl)-2-oxo-2,3-dihydro-1H-benzo[e][1,4]diazepine-3-carbamic acid benzyl ester N-Methyl piperazine (0.51 ml) was added to a stirred solution of intermediate 12 (0.5 g) in dry DCM (10 ml) at 23° under nitrogen. After 3 hours the mixture was poured into water (75 ml) and extracted with EA (50 ml × 3). The combined organic extracts were washed with saturated brine, dried and evaporated in vacuo. The crude product was purified by flash chromatography on silica (Merck 9385 -Et$_3$N deactivated) eluting with 2 to 4% MeOH in DCM to give the title compound as an orange foam (385 mg), m.p. 65°–70°.
T.l.c. SiO$_2$-Et$_3$N deactivated (2% MeOH-DCM) Rf 0.39.

INTERMEDIATE 20

2-{3-[3-(3-Methoxy-phenyl)-ureido]-5-methyl-2-oxo-2,3-dihydro-benzo[e][1,4]diazepin-1-yl}-N-methyl-N-phenyl-acetamide A solution of intermediate 4 (500 mg) in dry MeCN (10 ml) was treated with 3-methoxyphenylisocyanate (195 μl) and the mixture was stirred at 23° under nitrogen for 5 hours. DE (10 ml) was added and the resultant mixture was filtered, washing the filter-cake with hexane to give the title compound as a cream solid (599 mg), m.p. 215.
T.l.c. (EA) Rf 0.38

INTERMEDIATE 21

3-Amino-2,3-dihydro-1-(3.3-dimethyl-2-oxo-butyl)-5-methyl-2-oxo-1H-1,4-benzodiazpine (a) N-[5-Methyl-1-(3.3-dimethyl-2-oxo-butyl)-2-oxo-3.1-dihydro-benzo[e][1,4]diazepin-3-yl]-carbamic acid benzyl ester Sodium hydride (80% in oil, 235 mg) was added to a solution of Intermediate 2, (2 g) in dry DMF (20 ml) under nitrogen and cooled in an ice-bath. After 45 min, a solution of 1-bromopinacolone (1.23 g) in dry DMF (5 ml) was added and stirred for 2 h 20 min as the ice-bath was allowed to melt. The reaction mixture was partioned between water (150 ml) and EA (2×150 ml) and the combined EA extracts were washed with water (100 ml), saturated brine (100 ml) and dried. The solution was evaporated and the residue chromatographed with hexane-EA (1:2) as eluent to give the title compound (2.47 g) as a white foam, m.p. 68°.

b. 3-Amino-2,3-dihydro-1-(3.3-dimethyl-2-oxo-butyl)-5-methyl-2-oxo-1H-1,4-benzodiazpine A 3-necked flask was flushed thoroughly with nitrogen and charged successively with 5% palladium on carbon (50%) wet paste; 1.66 g) water (45 ml), a solution of Intermermediate 21a (2.42 g) in methanol (180 ml) and ammonium formate (1.09 g). The mixture was stirred at 40° under nitrogen for 1.5 h then cooled and filtered through hyflo. The filtrate was evaporated and the residue partioned between 2N sodium carbonate solution (100 ml) and EA (2×150 ml). The combined organic extracts were washed with saturated brine (100 ml), dried and evaporated to give the title compound (1.63 g) as a fawn solid, m.p. 96°–8°.
T.l.c. (9:1 DCM-MeOH) Rf 0.33.

INTERMEDIATE 22

N-[5-Methyl-1-(2-oxo-2-pyrrolidin-1-yl-ethyl)-2,oxo-1.3-dihydro-benzo[e][1,4]diazepin-3-yl]-carbamic add benzyl ester NaH (80% in oil; 102 mg) was added to a solution of intermediate 2(1.00 g) in dry DMF (10 ml) at 0°. The mixture was stirred at 0° for 0.5 h and a solution of 2-N-pyrrolidinyl-2-oxo-ethylbromide (596 mg) in DMF (1 ml) was added. The mixture was stirred at 23° for 4 h. Phosphate buffer (pH 6.5; 50 ml) was added and the mixture extracted with ethyl acetate (50 ml). The organic phase was washed with water (2×50 ml) and dried (Na$_2$SO$_4$). Solvent evaporation in vacuo gave a residue which was chromatographed with EA then MeOH-EA (1:9) as eluent to give the title compound (959 mg) as a white solid, m.p. 165°–6°.
T.l.c. (EA) Rf 0.16
I.r. (Solution in CHBr3) 3147; 2974; 2874; 1719; 1683; 1654; 1057; 1449: 1079; 765 cm$^{-1}$

INTERMEDIATE 23

N-[5-(Bromo-methyl)-1-(2-oxo-2-pyrrolidin-1-yl-ethyl)-2-oxo-1.3-dihydro-benzo[e][1,4]diazepin-3-yl]-carbamic acid benzyl ester A solution of intermediate 22(4.00 g) in DE (50 ml) and CHCl$_3$ (50 ml) under nitrogen at 23° was treated with 5,5-dibromobarbituric acid (1.32 g) and the mixture stirred at 23° for 18 h, MeOH (20 ml) and silica (Merck 9385;15 g) were added and the solvent evaporated in vacuo. The residue was chromatographed with MeOH-DCM (0.2:10) as eluent to give the title compound as a white solid (3.88 g).
T.l.c, (10:0.2 DCM-MeOH) Rf 0.36
I.r. 3389; 1733; 1686; 1662; 1650; 1596; 1330; 1217; 1200; 1084; 777 cm$^{-1}$

INTERMEDIATE 24

N-[5-(Morpholin-4-yl-methyl)-1-(2-oxo-2-pyrrolidin-1yl-ethyl)-2-oxo-1.3-dihydro-benzo[e][1,4]diazepin-3-yl]-carbamic acid benzyl ester A solution of intermediate 23 (3.78 g) in DMF (20 ml) under nitrogen at 23° was treated with morpholine (3.21 g) and the mixture was stirred for 1 h. Water was added and the mixture extracted with EA. The extract was washed with water and saturated brine then was dried (Na$_2$SO$_4$). The solvent was evaporated in vacuo and the residue purified by chromatography. Elution with DCM-MeOH (100:3) gave the title compound as a pale orange foam (1.095 g).
T.l.c. (100:3 DCM - MeOH) Rf 0.27
I.r. (KBr disc)3426; 2979; 1723; 1688; 1661; 1510; 1453; 1394; 1323; 1116; 1090; 929 cm$^{-1}$

INTERMEDIATE 25

3-Amino-5-(morpholin-4-yl-methyl)-1-(2-oxo-2-pyrrolidin-1-yl-ethyl)-1.3-dihydro-benzo-[e][1,4]diazepin-2-one A solution of intermediate 24 (3.584 g) in EtOH (100 ml) was hydrogenated over 10% palladium on carbon (500 mg) at 23°. After 3.5 h the mixture was filtered through hyflo and the filtrate evaporated in vacuo to give the title compound as a beige foam (2.536 g).
T.l.c. (9:1 DCM-MeOH) Rf 0.22
I.r (KBr disc) 3396; 2981; 1657; 1448; 1322; 1256; 1116; 865 cm$^{-1}$

INTERMEDIATE 26

Ethyl-(4-fluoro-phenyl)-amine

Iodoethane (3.6 ml) was added to a mixture of 4-fluoroaniline (4.26 ml) and potassium carbonate (6.9 g) in dry DMF (100 ml). After 18.5 h at 23°, the resulting suspension was poured into water (400 ml) and extracted with EA (400 ml). The organic extract was washed with water (200 ml) then saturated brine (200 ml), dried and evaporated. The residual oil was chromatographed with 2 to 3 to 4% EA in hexane as eluent to give the title compound (3.667 g) as a yellow oil.
T.l.c. (4:1 Hexane-EA) Rf 0.62

INTERMEDIATE 27

2-Bromo-N-ethyl-N-(4-fluoro-phenyl)-acetamide

A solution of bromoacetyl bromide (2.24 ml) in dry DCM (15 ml) was added dropwise over 20 min to a solution of intermediate 26 (3.58 g) and Et$_3$N (3.59 ml) in dry DCM (30 ml) at 0° under nitrogen. After 2.5 h at 0° the solution was partitioned between water (200 ml) and DCM (200+100 ml). The combined organic extracts were dried and evaporated and the residue chromatographed with 10 to 15 to 20% EA in hexane as eluent to give the title compound (2.641 g) as a pale orange oil.
T.l.c. (9:1 hexane-EA) Rf 0.15

INTERMEDIATE 28

N-(1-{[Ethyl-(4-fluoro-phenyl)-carbamoyl]-methyl}-5-methyl-2-oxo-1.3-dihydro-benzo[e][1,4]diazepin-3-yl)-carbamic acid benzyl ester NaH (80% in oil; 348 mg) was added to a solution of intermediate 2 (2.92 g) in dry DMF (30 ml) at 0° under nitrogen. After 1 h, the orange solution was treated with a solution of intermediate 27 (2.608 g) in dry DMF (10 ml). Stirring was continued at 0° for 2 h whereupon the solution was poured into water (200 ml) and extracted with EA (200+100 ml). The combined extracts were washed with saturated brine (200 ml), dried and evaporated. The residue was chromatographed with EA-DCM (4:1) as eluent to give the title compound (3.75 g) as a pale yellow foam.
T.l.c. (4:1 EA-DCM) Rf 0.26
I.r. (Solution in CHCl$_3$) 3425; 1724; 1671; 1515; 1510; 1248; 1094; 845 cm$^{-1}$

INTERMEDIATE 29

N-{1-[Ethyl-(4-fluoro-phenyl)-carbamoyl-methyl]-5-(morpholin-4-yl-methyl)-2-oxo-1.3-dihydro-benzo[e][4]diazepin-3-yl}-carbamic acid benzyl ester 5,5-Dibromobarbituric acid (765 mg) was added to a solution of intermedaite 28 (2.69 g) in CHCl$_3$ (30 ml) and DE (30 ml) at 23° under nitrogen. After 30 h morpholine (2.3 ml) was added and stirring continued for a further 16 h whereupon the cloudy orange solution was poured into water (100 ml). The layers were separated and the aqueous phase extracted with CHCl$_3$ (100 ml). The combined, dried organic extracts were evaporated and the residue chromatographed with EA-DCM (3:1) as eluent to give the title compound (2.22 g) as a crunchy orange foam.
T.l.c. (4:1 EA-DCM) Rf 0.17
I.r. (Solution in CHCl$_3$) 3621; 3425; 1726; 1672; 1510; 1233; 1202; 1116; 845 cm$^{-1}$

INTERMEDIATE 30

2-[3-Amino-5-(morpholin-4-yl-methyl)-2-oxo-2,3-dihydro-benzo[e][1,4]diazepin-1-yl]-N-ethyl-N-(4-fluoro-phenyl)acetamide A solution of intermediate 29(1.144 g) in absolute EtOH (25 ml) was hydrogenated at 23° and 1 atmosphere pressure in the presence of 10% palladium on charcoal as catalyst (160 mg). After stirring for 6 h and allowing to stand under hydrogen overnight the mixture was filtered through hyflo and the filtrate evaporated to give the title compound (879 mg) as a crunchy green-brown foam, m.p. 95°–9° dec.
T.l.c. (9:1 DCM-MeOH) Rf 0.18

INTERMEDIATE 31

3-(1.2.4-Oxadiazol-3-yl)-phenylamine

A solution of 3-(1,2,4-oxidazol-3-yl)nitrobenzene (3.0 g) in EA (50 ml) was hydrogenated at 1 atm. and 23° over Raney nickel (1 pipette-full). After 4.5 h the catalyst was removed by filtration through hyflo. The filtrate was evaporated to give a pale cream solid (2.57 g) identified as the hydroxylamine.
T.l.c. (1:1 EA-Hexane) Rf 0.27
A solution of the hydroxylamine (2.54 g) in EA (40 ml) was further hydrogenated at room temperature and pressure over Raney nickel (1 pipette-full). After 4.5 h the catalyst was removed by filtration through hyflo and the filtrate evaporated to give a yellow solid. Crystallization from EA gave pure product. The mother liquors were chromatographed with hexane—DE (3:1) as eluent to give more product which was combined with the crystallized material to give the title compound (548 mg) as a cream solid.
T.l.c. (2:1 DE-Hexane) Rf 0.35

EXAMPLE 1

2-{3-[3-(3-Cyano-phenyl)-ureido]-2-oxo-5-piperidin-1-ylmethyl-2,3-dihydro-benzo-[e][4.1]diazepin-1-yl}-N-methyl-N-phenyl-acetamide A solution of intermediate 6 (300 mg) in DCM (5 ml) at 23° under nitrogen was treated with piperidine (0.27 ml). After 2 hours the mixture was poured into water (75 ml) and extracted with EA (100 ml×2). The combined organic extracts were washed with saturated brine, dried and evaporated in vacuo. The crude product was partially purified by flash chromatography on silica (Merck 9385-Et$_3$N deactivated) eluting with 2% MeOH in DCM. Complete purification was obtained by flash chromatography on silica (Merck 9385-Et$_3$N deactivated) eluting with 1 to 2% MeOH in DCM to give the title compound as a cream solid (135 mg), m.p. 145–150°
I.r. 3260; 2222; 1704; 1686; 1591; 1383; 1223; 1125 cm$^{-1}$

EXAMPLE 2

2-{3-[3-(3-Cyano-phenyl)-ureido]-2-oxo-5-pyrrolidin-1-ylmethyl-2,3-dihydro-[e][1,4]diazepin-1-yl}-N-methyl-N-phenyl-acetamide A solution of intermediate 6 (300 mg) in DCM (5 ml) at 23° under nitrogen was treated with pyrrolidine (0.22 ml). After 2 hours the mixture was evaporated in vacuo to give a brown oil which was purified by flash chromatography on silica (Merck 9385-Et$_3$N deactivated) eluting with 2% MeOH in DCM. Product fractions, after evaporation in vacuo, were triturated with EA-hexane. The solid was dissolved in EA-THF (4:1; 100 ml) and the solution was washed with water and saturated brine then was dried and evaporated in vacuo to give the title compound as a pale peach solid (154 mg), m.p. 140°–145° dec.
T.l.c. Et$_3$N deactivated SiO$_2$ (2%MeOH-DCM) Rf 0.22
I.r. 3342; 2226; 1685; 1593; 1559; 1496; 1381 cm$^{-1}$

EXAMPLE 3

2-{-[3-(3-Cyano-phenyl)ureido]-5-(isopropylamino-methyl)-2-oxo-2,3-dihydro-benzo-[e][1,4]diazepin-1-yl}-N-methyl-N-phenyl-acetamide A solution of intermediate 6 (300 mg) in DCM (5 ml) at 23° under nitrogen was treated with isopropylamine (0.23 ml). After 2 hours the mixture was evaporated in vacuo to give an oil which was purified by flash chromatography on silica (Merck 9385-Et$_3$N deactivated) eluting with 2% MeOH-DCM. Trituration with EA-hexane gave a cream solid which was dissolved in EA-THF (4:1; 100 ml) and washed with water (100 ml) and saturated brine, dried and evaporated in vacuo to give the title compound as a cream solid (132 mg), m.p. 160° dec.
T.l.c. Et$_3$N deactivated SiO$_2$(2% MeOH-DCM) Rf 0.16
I.r. 3316; 2231; 1674; 1591; 1561; 1455; 1432; 1384; 1240; 1198 cm$^{-1}$

EXAMPLE 4

2-{3-[3-(3-Cyano-phenyl)-ureido]-2-oxo-5-[1,4]thiazinan-4-ylmethyl-2,3-dihydro-benzo[e][1,4]diazepin-1-y}-N-methyl-N-phenyl-acetamide A solution of intermediate 6 (1 g) in dry DCM (20 ml) was treated with thiomorpholine (0.90 ml) at 23° under nitrogen. After 2 hours the mixture was poured into water (75 ml) and extracted with EA (3×75 ml). The combined organic extracts were washed with saturated brine, dried and evaporated in vacuo. The crude product was purified by flash chromatography eluting with EA to give, after trituration with EA-hexane, the title compound as a white solid (458 mg), m.p. 165°.
T.l.c. Et$_3$N deactivated SiO$_2$ (EA) Rf 0.52
I.r. 3267; 2229; 1687; 1557; 1450; 1382; 1221 cm$^{-1}$

EXAMPLE 5

1-(3-Cyano-phenyl)-3-{1-[2-(cis-2.5-dimethyl-pyrrolidin-1-yl)-2-oxo-ethyl]-5-morpholin-4-ylmethyl-2-oxo-2,3-dihydro-1H-benzo[e][1,4[diazepin-3-yl}urea NaH (80% in oil; 23 mg) was added to a suspension of intermediate 9 (253 mg) in dry DMF (3 ml) at 0° under nitrogen. After 30 min the resulting solution was treated with a solution of 2-(cis-2,5-dimethylpyrrolidin-1-yl)-2-oxo-ethyl bromide (145 mg) in dry DMF (0.5 ml) and stirring was continued at 0° for 2.25 h and at 23° for 20 h. The dark solution was poured into water (20 ml) and extracted with EA (2×30 ml) then the combined extracts were washed with water (20 ml) then saturated brine (40 ml), dried and evaporated. Trituration of the residue with EA-DE gave the title compound (196 mg) as a white solid, m.p. 234°–5° dec.
T.l.c. (95:5 DCM-MeOH) Rf 0.26
I.r. 3263; 2224; 1685; 1650; 1590; 1557; 1449; 1378; 1115; 1001 cm$^{-1}$

EXAMPLE 6

2-{3-[3-(3-Cyano-phenyl)-ureido]-5-morpholin-4-ylmethyl-2-oxo-2,3-dihydro-benzo-[e][1,4]diazepin-1-yl}-N-(4-fluoro-phenyl)-N-methyl-acetamide NaH (80% in oil; 23 mg) was added to a suspension of intermediate 9 (250 mg) in dry DMF (3 ml) at 0° under nitrogen. After 40 min a solution of 2-bromo-N-(4-fluorophenyl)-N-methyl-acetamide (162 mg)in dry DMF (0.5 ml) was added to the resulting solution and stirring was continued at 23° for 22 h. The yellow solution was then poured into water (20 ml) and extracted with EA (2×30 ml) and the combined extracts were washed with water (20 ml) then saturated brine (40 ml) dried and evaporated. A solution of the residue in MeOH was preadsorbed onto silica and chromatographed with 0 to 1 to 2 to 3 to 4% MeOH in DCM as eluent to give the title compound (260 mg) as an orange solid, m.p. 182°–4° dec.
T.l.c. (95:5 DCM-MeOH) Rf 0.19
I.r. 3341; 2229; 1674; 1510; 1223; 1116 cm$^{-1}$

EXAMPLE 7

2-{3-[3-(3-Cyano-phenyl)-ureido]-5-morpholin-4-ylmethyl-2-oxo-2,3-dihydro-benzo[e][1,4]diazepin-1yl}-N-ethyl-N-phenyl-acetamide NaH (80% in oil; 23 mg) was added to a suspension of intermediate 9 (250 mg) in dry DMF (3 ml) at 0° under nitrogen. After 40 min a solution of 2-bromo-N-ethyl-N-phenyl acetamide (160 mg) in dry DMF (0.5 ml) was added to the resulting solution and stirring was continued at 23° for 22 h. The orange solution was then poured into water (20 ml) and extracted with EA (2×30 ml) and the combined extracts were washed with water (20 ml) then saturated brine (30 ml) dried and evaporated. Trituration of the residue with EA-DE gave the title compound (239 mg) as a white solid, m.p. 211°–2° dec.
T.l.c. (95:5 DCM-MeOH) Rf 0.26
I.r. 3294; 2225; 1684; 1666; 1456; 1203; 777 cm$^{-1}$

EXAMPLE 8

1-(3-Cyano-phenyl)-3-[1-(3,3-dimethyl-2-oxo-butyl)-5-morpholin-4-ylmethyl-2-oxo-2,3-dihydro-1H-benzo[e][1,4]diazepin-3-yl]-urea Morpholine (62 µl) was added to a suspension of intermediate 11 (72 mg) in dry DCM (2 ml) at 23° under nitrogen. After 1 h the mixture was poured into water (20 ml) and extracted with EA (20+15 ml). The combined extracts were washed with saturated brine (20 ml) dried and evaporated. The residue was triturated with EA-DE, filtered off and dried in vacuo to give the title compound (53 mg) as a white solid, m.p. 168°–9° dec.

T.l.c. (95:5 DCM-MeOH) Rf 0.26
I.r. 3279; 2229; 1688; 1455 cm$^{-1}$

EXAMPLE 9

2-{3-[3-(3-Methoxy-phenyl)-ureido]-5-morpholin-4-ylmethyl-2-oxo-2,3-dihydro-benzo[e][1,4]diazepin-1-yl}-N-methyl-N-phenyl-acetamide 3-Methoxyphenyl isocyanate (53 mg) was added to a solution of intermediate 14 (150 mg) in DCM (5 ml) under nitrogen. The solution was stirred at 23° for 3 h. The solvent was evaporated in vacuo and the residue purified by chromatography. Elution with MeOH-DCM (1:20) gave the title compound as a pale straw coloured solid (176 mg), m.p. 164°–6° dec.
T.l.c. (1:20 MeOH-DCM) Rf 0.25
I.r. (Solution in CHCl3) 3431; 1670; 1599; 1495; 1454; 1425; 1392; 1289; 1158; 1116 cm$^{-1}$.

EXAMPLE 10

N-Methyl-2-[5-morpholin-4-ylmethyl-2-oxo-3-(3-phenyl-ureido)-2,3-dihydro-benzo[e][1,4]diazepin-1-yl]-N-methyl-N-phenyl-acetamide Phenyl isocyanate (42 mg) was added to a solution of intermediate 14 (150 mg) in MeCN (5 ml) under nitrogen and the mixture was stirred at 23 for 2 h. DE was added and the mixture was filtered to give the title compound as a white solid (160 mg), m.p. 157°–8° dec.
T.l.c. (1:20 MeOH-DCM) Rf 0.33
I.r. (Solution in CHCl$_3$)3430; 1670; 1599; 1498; 1452; 1392; 1311; 1292; 1116; 1002 cm$^{-1}$.

EXAMPLE 11

N-Methyl-2-{5-morpholin-4-ylmethyl-2-oxo-3-[3-(3-trifluoromethyl-phenyl)-ureido]-2,3-dihydro-benzo[e][1,4]diazepin-1-yl}-N-phenyl-acetamide 3-Trifluoromethylphenyl isocyanate (103μl) was added dropwise to a stirred solution of intermediate 14 (300 mg) in dry DCM (3 ml). The mixture was stirred at room temperature under nitrogen for 18 hrs. Purification by column chromatography eluting with DCM-MeOH-. 880 ammonia (94.5:5:0.5), gave the title compound (87 mg) as a white solid, m.p. 190° dec.
T.l.c. (94.5:5:0.5 DCM-MeOH-880 ammonia) Rf 0.22
I.r. 2924; 2854; 1688; 1671; 1450; 1339; 1116 cm$^{-1}$

EXAMPLE 12

(3-{3-[1-(Methyl-phenyl-carbamoylmethyl)-5-morpholin-4-ylmethyl-2-oxo-2,3-dihydro-1H-benzo[e][1,4]diazepin-3-yl]-ureido}-phenyl)-carbamic acid tert-butyl ester Carbonyl diimidazole (97 mg) was added to a solution of intermediate 14 (230 mg) in THF (10 ml) under nitrogen and the mixture was stirred a 23 for 1 h. (3-Amino-phenyl)-carbamic add t-butyl ester (114 mg) was added and the mixture was heated under reflux for 18 h. The mixture was cooled to 23 and was partitioned between water and EA. The organic phase was dried (Na$_2$SO$_4$) and the solvent evaporated in vacuo to give a residue which was purified by chromatography. Elution with MeOH-DCM (1:20) gave the title compound as a straw coloured solid (78 mg).
T.l.c. (1:20 MeOH-DCM) Rf 0.32
Mass spectrum MH$^+$ (observed) 656

EXAMPLE 13

2-{3-[3-(3-Amino-phenyl)-ureido]-5-morpholin-4-ylmethyl-2-oxo-2,3-dihydro-benzo[e][1,4]diazepin-1-yl}-N-methyl-N-phenyl-acetamide A solution of Example 12 (70 mg) in DCM (5 ml) was treated with trifluoroacetic add (0.3 ml) and stirred for 1 h. EA was added, the mixture washed with 2N sodium carbonate solution, dried (Na$_2$SO$_4$) and evaporated in vacuo. The residue was triturated with DE to give the title compound as a beige solid (31 mg), m.p. 158°–60°.
T.l.c. (1:20 MeOH-DCM) Rf 0.22
I.r. 3353; 1667; 1613; 1596; 1556; 1496; 1321; 1204; 1115; 773 cm$^{-1}$.

EXAMPLE 14

(+)-2-{3-[3-(3-Methoxy-phenyl)-ureido]-5-morpholin-4-ylmethyl-2-oxo-2.3-dihydro-benzo[e][1,4]diazepin-1-yl}-N-methyl-N-phenyl-acetamide 3-Methoxyphenyl isocyanate (106 mg) was added to a stirred solution of intermediate 14 (300 mg) in DCM (10 ml) under nitrogen and the mixture was stirred at 23° for 2 h. The solvent was evaporated in vacuo and the residue purified by chromatography. Elution with MeOH-DCM (1:20) gave a straw coloured solid (205 mg) a portion. (75 mg) of which was further purified by chiral h.p.l.c. to give the title compound as a white solid (26 mg), m.p. 169–70 dec.
T.l.c. (1:20 MeOH-DCM) Rf 0.25
I.r. (Solution in CHCl$_3$) 3431; 1670; 1600; 1496; 1454; 1427; 1289; 1158; 1116; 1002 cm$^{-1}$
H.p.l.c. Column: CHIRALCEL-OD 25 cm × 4.6 mmid
Eluent: EtOH-Hexane (1:1)
Flow: 1 ml/min.
Wavelength: 230 nm
Temperature: 23°
R$_t$: 4.96 min

EXAMPLE 15

(+)2-{3-[3-(3-Methoxy-phenyl)-ureido]-5-morpholin-4-ylmethyl-2-oxo-2,3-dihydro-benzo[e][1,4]diazepin-1-yl}-N-methyl-N-phenyl-acetamide A solution of intermediate 18 (189 mg) in chloroform (8 ml) and DE (3 ml) under nitrogen was treated with 5,5-dibromobarbituric add (56 mg) and the mixture stirred at 23° in the dark for 18 h. Morpholine (68 mg) was added and the mixture was stirred for 2 h at 23°. The mixture was partitioned between EA and phosphate buffer (pH6.5). The organic phase was dried (Na$_2$SO$_4$) and the solvent evaporated in vacuo to give a residue which was purified by chromatography. Elution with EA then MeOH-DCM (1:20) gave the title compound as a white solid (147 mg), m.p. 164°–6° dec.
T.l.c. (1:20 MeOH-DCM) Rf 0.35
I.r. 3339; 1668; 1598; 1549; 1290; 1203; 1156; 1115; 771; 703 cm$^{-1}$

EXAMPLE 16

2-{3-[3-(3-Cyano-phenyl)-ureido]-5-(4-methyl-piperazin-1-ylmethyl)-2-oxo-2,3-dihydro-benzo[e][1,4]diazepin-1-yl}-N-methyl-N-phenyl-acetamide A solution of intermediate 19 (352 mg) in EtOH (20 ml) was hydrogenated at 23° and 1 atm pressure using 10% palladium on carbon (80 mg) as a catalyst. After 7 hours the mixture was filtered through hyflo and evaporated to give crude amine (319 mg) as an orange-red oil. This was redissolved in dry MeCN (3 ml) and treated with 3-cyanophenyl isocyanate (85 mg) at 23° under nitrogen. After 2 hours the mixture was evaporated in vacuo to give a red oil which was purified by flash chromatography on silica (Merck 9385-Et$_3$N deactivated) eluting with 2 to 5 to 10% MeOH in DCM. Trituration with DE-hexane gave the title compound as a cream solid (171 mg), m.p. 152°–155°.
T.l.c. SiO$_2$-Et$_3$N deactivated (5% MeOH-DCM) Rf 0.20.
I.r. 3338; 2228; 1671; 1594; 1557; 1496; 1455 cm$^{-1}$.

EXAMPLE 17

2-{3-[3-(3-Methoxy-phenyl)-ureido]-5-(2-dimethylamino-ethyl)-2-oxo-2,3-dihydro-benzo[e][1,4]diazepin-[-yl}-N-methyl-N-phenyl-acetamide A mixture of intermediate 20 (100 mg) and Eschenmoser's salt (46 mg) in dimethoxyethane (5 ml) was heated to reflux for 4 hours then was poured into EA (50 ml) and extracted with 2N HCl (25 ml×2). The combined aqueous extracts were basified to pH8 with 2N Na$_2$CO$_3$ solution then extracted with EA (30 ml×2). The combined organic extracts were dried and evaporated in vacuo. The crude product was purified by flash chromatography on silica (Merck 9385-Et$_3$N deactivated) eluting with 2 to 3 to 4 to 5% MeOH in DCM to give the title compound as a cream solid (31 mg), m.p. 134°.
T.l.c. SiO$_2$-Et$_3$N deactivated (5% MeOH-DCM) Rf 0.13.
I.r. (Solution in CHCl$_3$) 2954; 1670; 1600; 1495; 1455; 1158; cm$^{-1}$.

EXAMPLE 18

2-{3-[3-(3-Cyano-phenyl)-ureido]-5-morpholin-4-ylmethyl-2-oxo-2,3-dihydro-benzo[e][1,4]diazepin-1-yl}-N-methyl-N-phenyl-acetamide A solution of intermediate 14 (113 mg) in DCM (5 ml) was treated with 3-cyanophenyl isocyanate (39 mg) and the mixture stirred at 23° under nitrogen for 18 h. The solvent was removed in vacuo and the residue chromatographed with EA-EtOH (10:0.5) s eluent to give the title compound (64 mg) as a white solid, m.p. 165°–7°.
T.l.c. (10:0.5 EA-EtOH) Rf 0.24
I.r. 3264; 2225; 1677; 1460; 1378 cm$^{-1}$.

EXAMPLE 19

1-[5-(Morpholin-4-yl-methyl)-2-oxo-1-(2-oxo-2-pyrrolidin-1-yl-ethyl)-2,3-dihydro-benzo[e][1,4]diazepin-3-yl]-3-(3-oxazol-5-yl-phenyl)-urea A solution of 3-(oxazol-5-yl)phenylamine (250 mg) in THF (6 ml) under nitrogen at 0° was treated with Et$_3$N (79 mg) followed by triphosgene (77 mg). More Et$_3$N (79 mg) was added and the mixture was stirred at 0° for 0.5 h. A solution of intermediate 25 (125 mg) in THF (5 ml), was added and the mixture was stirred at 23° for 2 h. Phosphate buffer (pH6.5; 30 ml) was added and the mixture extracted with EA (30 ml). The organic phase was dried (Na$_2$SO$_4$) and the solvent evaporated in vacuo. The residue was chromatographed. Elution with MeOH-EA (0.5:10) then MeOH-DCM (0.5:10) gave the title compound as a pale straw solid (199 mg), m.p. 208°–9°.
T.l.c. (9:1 DCM-MeOH) Rf 0.42
I.r. 3284; 1683; 1663; 1551; 1499; 1324; 1205; 1116; 1003; 774 cm$^{-1}$

EXAMPLE 20

1-[5-(Morpholin-4-yl-methyl)-2-oxo-1-(2-oxo-2-pyrrolidin-1-yl-ethyl)-2,3-dihydro-1H-benzo[e][1,4]diazepin-3-yl]-3-[3-(1.2.4-oxadiazol-3-yl)-phenyl]-urea A solution of intermediate 31 (100 mg) in THF (6 ml) at 0° under nitrogen was treated with Et$_3$N (63 mg). Triphosgene (62 mg) was then added followed by more Et$_3$N (62 mg). The mixture was stirred at 0° for 0.5 h. A solution of Intermediate 25 (200 mg) in THF (5 ml) was added and the mixture stirred at 23° for 2 h. Phosphate buffer (pH 6.5; 30 ml) was added and the mixture extracted with DCM (30 ml). The organic phase was dried (Na$_2$SO$_4$) and the solvent evaporated in vacuo to give a residue which was chromatographed with MeOH-DCM (0.5:10 to 1:10) as eluent to give the title compound (97 mg) as a pale straw coloured solid, m.p. 197°–9° dec.
T.l.c. (10:0.5 DCM-MeOH) Rf 0.27
I.r. (Solution in DMSO) 1684; 1656; 1615; 1599; 1568; 1540; 1510; 1347; 1204 cm$^{-1}$

EXAMPLE 21

N-Ethyl-N-(4-fluoro-phenyl)-2-{3-[3(4-fluoro-phenyl)-ureido]-5-(morpholin-4-yl-methyl)-2-oxo-2,3-dihydro-benzo[e][1,4]diazepin-1-yl}-acetamide 4-Fluorophenyl isocyanate (49 mg) in dry MeCN (0.5 ml) was added to a solution of intermediate 30(150 mg) in dry MeCN (1 ml) at 23° under nitrogen. After 1 h DE (3 ml) was added and the solid filtered off and dried in vacuo to give the title compound (100 mg) as a white solid, m.p. 197° dec.
T.l.c. (9:1 DCM-MeOH) Rf 0.51
I.r. 3340; 2926; 1672; 1509; 1461; 1378 cm$^{-1}$

EXAMPLE 22

(+)-2-{3-[-3-(3-Methoxy-phenyl)-ureido]-5-morpholin-4-ylmethyl-2-oxo-2,3-dihydro-benzo[e][-1,4]diazepin-1-yl}-N-methyl-N-phenyl-acetamide hydrochloride salt A solution of the (+)-2-{3-[3-(3-Methoxy-phenyl)-ureido]-5-morpholin-4-ylmethyl 2-oxo-2,3-dihydro-benzo [e][1,4]diazepin-1-yl}-N-methyl-N-phenyl-acetamide (200 mg) in dry DCM (20 ml) under nitrogen was treated with 1M hydrogen chloride in diethyl ether (0.77 ml) and the solution was stirred for 5 min. The solvent was removed in vacuo and the residue azeotroped with toluene (2×10 ml) to give the title compound (215 mg) as a pale straw coloured solid, m.p. 160°–170° dec.

PHARMACY EXAMPLES

Tablets

| a. | | |
|---|---|---|
| | Active ingredient | 50 mg |
| | Lactose anhydrous USP | 163 mg |
| | Microcrystalline Cellulose NF | 69 mg |
| | Pregelatinised starch Ph.Eur. | 15 mg |
| | Magnesium stearate USP | 3 mg |
| | Compression weight | 300 mg |

The active ingredient, microcrystalline cellulose, lactose and pregelatinised starch are sieved through a 500 micron sieve and blended in a suitable mixer. The magnesium stearate is sieved through a 250 micron sieve and blended with the active blend. The blend is compressed into tablets using suitable punches.

| b. | | |
|---|---|---|
| | Active ingredient | 50 mg |
| | Lactose monohydrate USP | 120 mg |
| | Pregelatinised starch Ph.Eur. | 20 mg |
| | Crospovidone NF | 8 mg |
| | Magnesium stearate USP | 3 mg |
| | Compression weight | 200 mg |

The active ingredient, lactose and pregelatinised starch are blended together and granulated with water. The wet mass is dried and milled. The magnesium stearate and Crospovidone are screened through a 250 micron sieve and blended with the granule. The resultant blend is compressed using suitable tablet punches.

Capsules

| a. | | |
|---|---|---|
| | Active ingredient | 50 mg |
| | Pregelatinised Starch Ph.Eur. | 148 mg |
| | Magnesium stearate USP | 2 mg |
| | Fill weight | 200 mg |

The active ingredient and pregelatinised starch are screened through a 500 micron mesh sieve, blended together and lubricated with magnesium stearate (meshed through a 250 micron sieve). The blend is filled into hard gelatin capsules of a suitable size.

| b. | | |
|---|---|---|
| | Active ingredient | 50 mg |
| | Lactose monohydrate USP | 223 mg |
| | Povidone USP | 12 mg |
| | Crospovidone NF | 12 mg |
| | Magnesium stearate | 3 mg |
| | Fill weight | 300 mg |

The active ingredient and lactose are blended together and granulated with a solution of Povidone. The wet mass is dried and milled. The magnesium stearate and Crospovidone are screened through a 250 micron sieve and blended with the granule. The resultant blend is filled into hard gelatin capsules of a suitable size.

A preferred active ingredient for use in the pharmacy examples is the compound of Example 14.

CCK-B- Receptor Binding

The binding affinity of the compounds of the invention for the CCK-B receptor (guinea pig cortex assay) was determined using the procedure of G Dal Forno et al J. Pharmacol. Exp & Ther. 261—1056–1063. The pKi values determined with respresentative compounds of invention were as follows:

| Compound Ex No | pKi |
|---|---|
| 1 | 9 |
| 2 | 8.4 |
| 3 | 8.6 |
| 4 | 8.8 |
| 5 | 8.5 |
| 6 | 8.7 |
| 7 | 8.8 |
| 8 | 8.8 |
| 9 | 8.9 |
| 10 | 9.1 |
| 11 | 9.3 |
| 13 | 8.2 |
| 14 | 9 |
| 16 | 8.3 |
| 17 | 8.6 |
| 18 | 8.9 |
| 19 | 8.5 |

The compounds of the invention are essentially non-toxic and therapeutically useful doses. Thus for example no untoward effects were observed when the compound of Example 14 was given to rats and dogs at doses at which the compound exhibits CCK-B antagonist activity.

We claim:

1. A compound of formula (I)

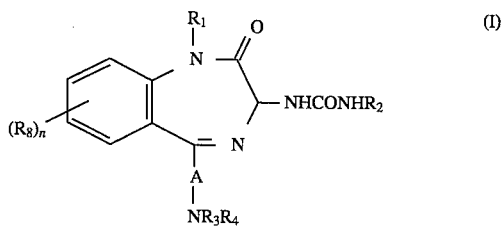

and physiologically acceptable salts thereof, wherein:

$R_1$ represents $CH_2CONR_5R_6$ or $CH_2COR_7$;

$R_2$ represents a phenyl group optionally substituted by one or two substituents selected from the group consisting of halogen, $C_{1-4}$alkyl, nitro, cyano, trifluoromethyl, trifluoromethoxy, $C_{1-4}$alkylthio, $C_{1-4}$alkylsulphinyl, $C_{1-4}$alkylsulphonyl, amino, substituted amino, hydroxy, $C_{1-4}$alkoxy, methylenedioxy, $C_{1-4}$alkoxycarbonyl, oxazolyl and oxadiazolyl;

A represents a $C_{1-4}$ straight or branched alkylene chain;

$R_3$ and $R_4$ independently represent hydrogen or $C_{1-4}$alkyl, or $R_3$ and $R_4$ together with the nitrogen atom to which they are attached form a saturated 5–7 membered heterocyclic ring selected from the group consisting of pyrrolidino, piperidino, hexamethylenimino, morpholino, thiomorpholino and oxides thereof, piperazino, N-methylpiperazino and N-$C_{1-4}$alkoxycarbonyl piperazino;

$R_5$ represents hydrogen or $C_{1-4}$alkyl;

$R_6$ represents $C_{1-4}$alkyl or phenyl which is optionally substituted by halogen; or $R_5$ and $R_5$ together with the nitrogen atom to which they are attached represent a saturated 5–7 membered heterocyclic ring selected from the group consisting of pyrrolidino, piperidino and hexamethylenimino which may be substituted by one or two methyl groups or by a group selected from the group consisting of:

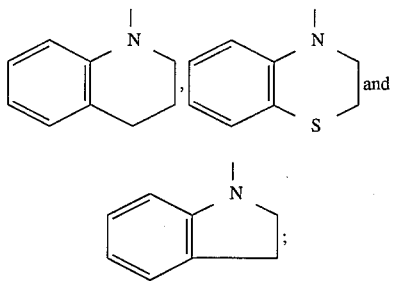

$R_7$ represents $C_{1-4}$alkyl, phenyl or phenyl substituted by a methyl group;

$R_8$ represents hydrogen or a halogen atom; and n is zero, 1 or 2.

2. A compound as claimed in claim 1 wherein $R_1$ is $CH_2CONR_5R_6$ wherein $R_5$ represents methyl or ethyl and $R_6$ represents phenyl optionally substituted by halogen, or $NR_5R_6$ represents a saturated heterocyclic ring selected from the group consisting of pyrrolidino, 2,5-dimethylpyrrolidino, 3,3-dimethylpyrrolidino, piperidino, 3,3-dimethylpiperidino and 1-tetrahydroquinolino.

3. A compound as claimed in claim 1 wherein $R_2$ is phenyl or phenyl substituted by one or two groups selected from the group consisting of halogen, $C_{1-4}$alkyl, $C_{1-4}$alkoxy, amino, cyano, hydroxy, trifluoromethyl, oxazolyl and 1,2,4-oxadiazol-3-yl.

4. A compound as claimed in claim 1 wherein $R_2$ is phenyl substituted by fluorine, oxazol-5-yl or methoxy.

5. A compound as claimed in claim 1 wherein A is a methylene chain.

6. A compound as claimed in claim 1 wherein $NR_3R_4$ represents a pyrrolidino, piperidino, hexamethylenimino, morpholino, thiomorpholino or N-methylpiperazino group.

7. A compound as claimed in claim 1 wherein $NR_3R_4$ is morpholino.

8. A compound as claimed in claim 1 wherein $R_6$ is hydrogen.

9. 2-{3-[3-(3-Methoxy-phenyl)-ureido]-5-morpholin-4-ylmethyl-2-oxo-2,3-dihydro-benzo [e][1,4]diazepin-1-yl}-N-methyl-N-phenyl-acetamide, the (+) enantiomer thereof and physiologically acceptable salts thereof.

10. A compound selected from the group consisting of:

N-Methyl-2-[5-morpholin-4-ylmethyl-2-oxo-3-(3-phenyl-ureido)-2,3 -dihydro-benzo[e][1,4]diazepin-1-yl]-N-phenyl-acetamide;

N-Methyl-2-{5-morpholin-4-ylmethyl-2-oxo-3-[3-(3-trifluoromethyl -phenyl)-ureido]-2,3- dihydro-benzo[e][1,4]diazepin-1-yl}-N-phenyl-acetamide;

2-{3-[3-(3-Cyano-phenyl)-ureido]-5-morpholin-4-ylmethyl-2-oxo-2, 3-dihydro-benzo[e][1,4]diazepin-1-yl}-N-methyl-N-phenyl-acetamide;

1 -[5-(Morpholin-4-yl-methyl)-2-oxo-1-(2-oxo-2-pyrrolidin-1-yl-ethyl)-2,3-dihydro-1H-benzo[e][1,4]diazepin-3-yl]-3-(3-oxazol-5-yl-phenyl)-urea;

N-Ethyl-N-(4fluoro-phenyl)2-{3 -[3-(4fluoro-phenyl)-ureido]5(morpholin4-yl-methyl)-2-oxo-2,3-dihydro-benzo[e][1,4]diazepin-1-yl}-acetamide; enantiomers thereof; and physiologically acceptable salts thereof.

11. A pharmaceutical composition for treatment of a mammal including man for conditions where modification of the effects of gastrin; and/or CCK is a therapeutic benefit comprising an effective amount of a compound as defined in claim 1 in admixture with one or more physiologically acceptable carriers or excipients.

12. A method of treatment of a mammal including man for conditions where modification of the effects of gastrin and or CCK is a therapeutic benefit comprising administration of an effective amount of a compound as defined in claim 1.

* * * * *